(12) United States Patent
Onishi

(10) Patent No.: US 11,921,079 B2
(45) Date of Patent: Mar. 5, 2024

(54) GAS SENSOR

(71) Applicant: NGK INSULATORS, LTD., Nagoya (JP)

(72) Inventor: Ryo Onishi, Iwakura (JP)

(73) Assignee: NGK INSULATORS, LTD., Nagoya (JP)

( * ) Notice: Subject to any disclaimer, the term of this patent is extended or adjusted under 35 U.S.C. 154(b) by 41 days.

(21) Appl. No.: 17/189,293

(22) Filed: Mar. 2, 2021

(65) Prior Publication Data
US 2021/0278363 A1 Sep. 9, 2021

(30) Foreign Application Priority Data

Mar. 9, 2020 (JP) ................................ 2020-039651

(51) Int. Cl.
| | | |
|---|---|---|
| *G01N 27/407* | (2006.01) | |
| *G01N 27/406* | (2006.01) | |
| *G01N 33/00* | (2006.01) | |

(52) U.S. Cl.
CPC ..... *G01N 27/4077* (2013.01); *G01N 27/4067* (2013.01); *G01N 33/0037* (2013.01)

(58) Field of Classification Search
CPC ........... G01N 27/4077; G01N 27/4067; G01N 33/0037; G01N 27/41; G01N 27/4071;
(Continued)

(56) References Cited

U.S. PATENT DOCUMENTS

| | | | | |
|---|---|---|---|---|
| 2002/0003088 A1* | 1/2002 | Ozawa | ............... | G01N 27/4077 204/424 |
| 2003/0094368 A1* | 5/2003 | Yamada | ............. | G01N 27/4077 204/431 |

(Continued)

FOREIGN PATENT DOCUMENTS

| | | |
|---|---|---|
| JP | 2001-281208 A | 10/2001 |
| JP | 2011-117935 | 6/2011 |

(Continued)

OTHER PUBLICATIONS

Japanese Office Action received in corresponding Japanese Application No. 2020-039651 dated Jul. 4, 2023.

*Primary Examiner* — Joshua L Allen
*Assistant Examiner* — Shizhi Qian
(74) *Attorney, Agent, or Firm* — MATTINGLY & MALUR, PC

(57) ABSTRACT

A gas sensor sensing a sensing target gas component contained in a measurement gas and identifying concentration of the sensing target gas component includes: a sensor element having an inlet for the measurement gas on one end portion, and including: an element base made of an oxygen-ion conductive solid electrolyte; a heater buried in the element base; and a porous leading-end protective layer covering a predetermined range of the element base on the one end portion; and a metallic member within which the sensor element is fixedly disposed, wherein a minimum distance between the sensor element and an inner surface of the metallic member is 0.20 mm or more and 0.95 mm or less, and a portion of the inner surface of the metallic member closest to the sensor element has an arithmetic average roughness of 5 μm or less.

14 Claims, 3 Drawing Sheets

(58) Field of Classification Search
CPC . G01N 27/4074; G01N 27/4075; Y02A 50/20
See application file for complete search history.

(56) References Cited

U.S. PATENT DOCUMENTS

| | | | |
|---|---|---|---|
| 2011/0094883 A1* | 4/2011 | Ito | G01N 27/4077 |
| | | | 204/429 |
| 2014/0130572 A1* | 5/2014 | Otsuka | G01N 27/4077 |
| | | | 73/23.31 |
| 2015/0268187 A1* | 9/2015 | Adachi | G01N 27/4078 |
| | | | 204/424 |
| 2016/0076919 A1 | 3/2016 | Murakami et al. | |
| 2016/0282298 A1* | 9/2016 | Hino | G01N 33/0036 |
| 2016/0370312 A1 | 12/2016 | Adachi et al. | |
| 2017/0059512 A1* | 3/2017 | Tahira | G01N 27/409 |
| 2017/0138895 A1* | 5/2017 | Iwamoto | G01M 15/102 |
| 2017/0284958 A1* | 10/2017 | Watanabe | G01N 27/4074 |
| 2017/0363596 A1* | 12/2017 | Adachi | G01N 27/4077 |

FOREIGN PATENT DOCUMENTS

| | | | | |
|---|---|---|---|---|
| JP | 2012093330 A | * | 5/2012 | |
| JP | 2014-098590 | | 5/2014 | |
| JP | 2015-178988 A | | 10/2015 | |
| JP | 2016-065852 A | | 4/2016 | |
| JP | 6313075 B2 | * | 4/2018 | |
| JP | 2019-168327 A | | 10/2019 | |
| WO | 2014/192945 A1 | | 12/2014 | |
| WO | WO-2016080176 A1 | * | 5/2016 | ......... G01N 27/4072 |

* cited by examiner

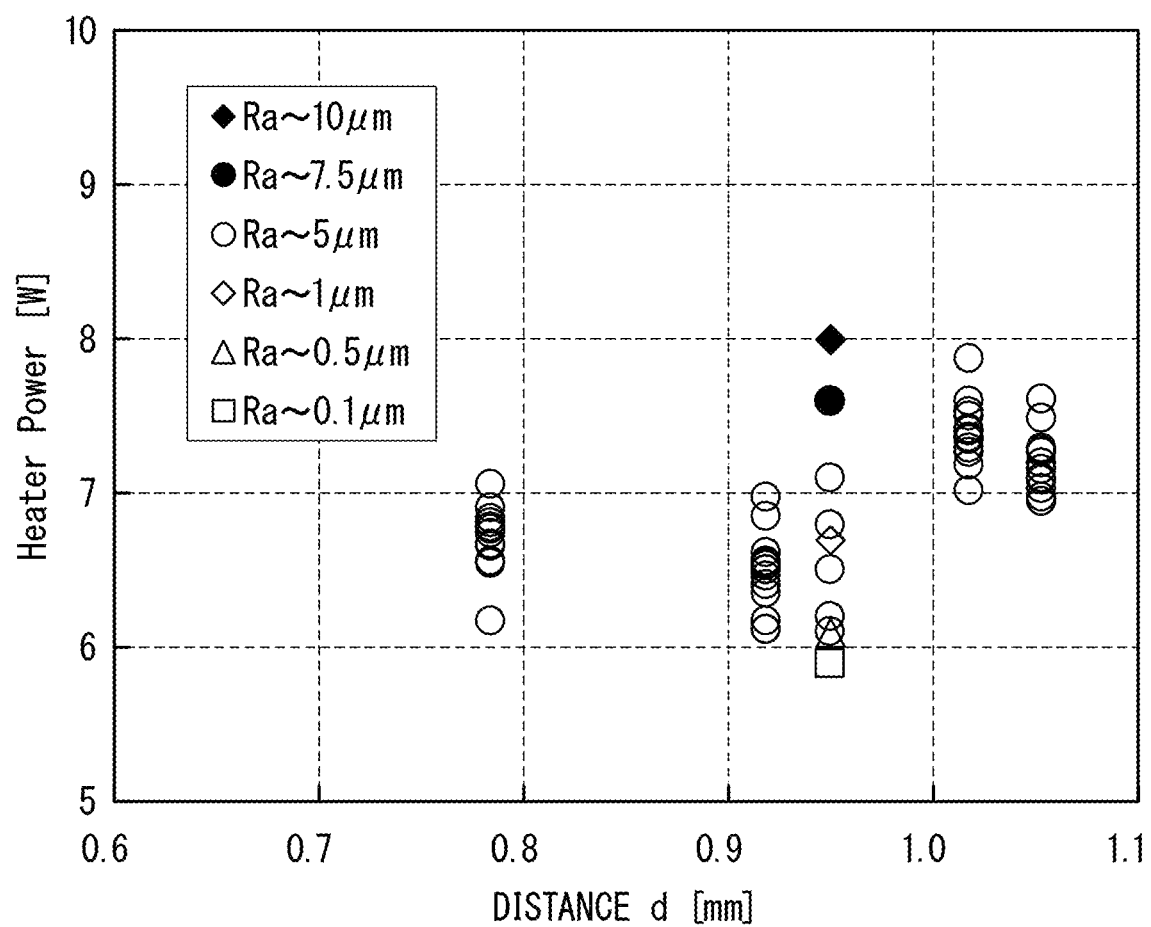

GAS SENSOR

CROSS-REFERENCE TO RELATED APPLICATION

The present application claims priority from Japanese application JP2020-039651, filed on Mar. 9, 2020, the contents of which is hereby incorporated by reference into this application.

BACKGROUND OF THE INVENTION

Field of the Invention

The present invention relates to a gas sensor, and, in particular, to suppression of power applied to a heater included in a sensor element.

Description of the Background Art

As a gas sensor for determining the concentration of a desired gas component contained in a measurement gas, such as an exhaust gas from an internal combustion engine, a gas sensor that includes a sensor element made of an oxygen-ion conductive solid electrolyte, such as zirconia ($ZrO_2$), and including some electrodes on the surface and the inside thereof has been widely known. As the sensor element, a sensor element having an elongated planar shape and including a protective layer formed of a porous body (porous protective layer) in an end portion in which a part for introducing the measurement gas is provided has been known (see Japanese Patent Application Laid-Open No. 2016-65852, for example).

In a sensor element as disclosed in Japanese Patent Application Laid-Open No. 2016-65852, the concentration of the desired gas component is identified based on a current flowing through the solid electrolyte when the measurement gas having been introduced through a gas inlet into an internal chamber is pumped by an electrochemical pump cell.

The protective layer is provided to the surface of such a sensor element to secure water resistance of the sensor element when the gas sensor is in use. Specifically, the protective layer is provided to prevent, in a case where water droplets adhere to the surface of the sensor element in a state of being heated by a heater located within the sensor element, water-induced cracking of the sensor element under the action of thermal shock caused by heat (cold) from the water droplets on the sensor element.

In such a gas sensor, the sensor element is disposed within a tubular housing, and fixed by ceramic parts, ceramic powders (a ceramic green compact), and the like. Furthermore, the gas sensor includes a protective cover for protecting the vicinity of an end portion of the sensor element in which the gas inlet is provided, mainly to prevent adherence of water generated at the start of an engine to the sensor element and entry of the water into the sensor element in a case where the gas sensor is attached to an exhaust pipe of an automobile in order to measure a desired gas component contained in an exhaust gas from the automobile, for example (see Japanese Patent Application Laid-Open No. 2019-168327, for example).

At assembly of parts of the gas sensor, a predetermined clearance is typically secured between the housing and the sensor element in view of the accuracy of assembly.

On the other hand, when the gas sensor is in use, the sensor element is heated to a predetermined temperature by the heater located within the sensor element to activate the solid electrolyte. A heat retaining effect produced by radiation from the housing, the protective cover, and the like as metallic parts is expected at the time. If an excessive clearance is secured at the assembly, however, there arises a problem that power that the heater requires to sufficiently obtain the heat retaining effect increases, and, as a result, a load on the heater increases to reduce the life of the heater.

The degree of the heat retaining effect is dependent also on properties (e.g., the thickness and the porosity) of a leading-end protective layer.

SUMMARY

The present invention relates to a gas sensor, and is, in particular, directed to suppression of power applied to a heater included in a sensor element.

According to the present invention, a gas sensor sensing a sensing target gas component contained in a measurement gas and identifying concentration of the sensing target gas component includes: a sensor element having an inlet for the measurement gas on one end portion, and including: an element base made of an oxygen-ion conductive solid electrolyte; a heater buried in the element base; and a porous leading-end protective layer covering a predetermined range of the element base on the one end portion; and a metallic member within which the sensor element is fixedly disposed, wherein a minimum distance between the sensor element and an inner surface of the metallic member is 0.20 mm or more and 0.95 mm or less, and a portion of the inner surface of the metallic member closest to the sensor element has an arithmetic average roughness of 5 µm or less.

The effect of retaining heat of the sensor element produced by radiation from the metallic member is thereby desirably obtained at heating of the sensor element to a predetermined driving temperature by the heater when the gas sensor is in use, so that power of the heater required at heating is suppressed, and the life of the heater and further the life of the gas sensor is extended.

It is thus an object of the present invention to achieve a gas sensor allowing for suppression of power applied to a heater when the gas sensor is in use.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a distribution chart showing a relationship among a distance d, an inner-surface roughness Ra of a housing 302, and heater power.

DESCRIPTION OF THE PREFERRED EMBODIMENTS

<Overview of Sensor Element and Gas Sensor>

Figure 1:
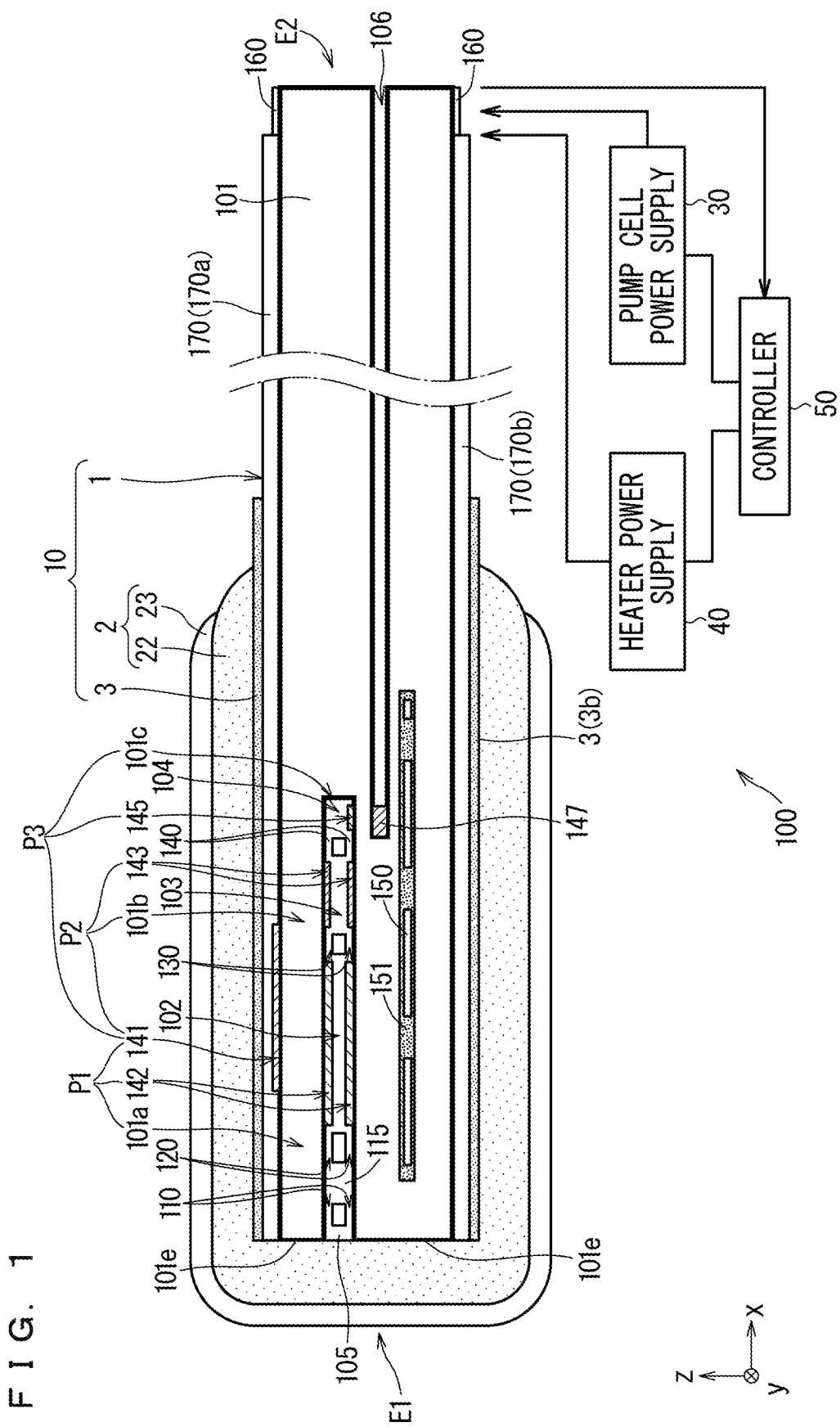
FIG. 1 is a schematic view of a configuration of a gas sensor 100.

FIG. 1 is a schematic view of a configuration of a gas sensor 100 according to the present embodiment. FIG. 1 includes a cross-sectional view taken along a longitudinal direction of a sensor element (gas sensor element) 10. The sensor element 10 is a ceramic structured body as a main component of the gas sensor 100 sensing a predetermined gas component in a measurement gas, and measuring the concentration thereof. The sensor element 10 is a so-called limiting current type gas sensor element. A right-handed xyz coordinate system having the longitudinal direction, a width direction, and a thickness direction of the sensor element 10 respectively as an x-axis, a y-axis, and a z-axis has been attached to FIG. 1 (the same applies to FIG. 2).

In addition to the sensor element 10, the gas sensor 100 mainly includes a pump cell power supply 30, a heater power supply 40, and a controller 50.

In the actual gas sensor 100, the sensor element 10 is housed in a housing, and has one end portion E1 covered with a protective cover (see FIG. 2), which is not illustrated in FIG. 1. Details of them will be described later.

As illustrated in FIG. 1, the sensor element 10 has a configuration in which a portion of an elongated planar element base 1 on the one end portion E1 is covered with a porous leading-end protective layer 2.

The element base 1 includes an elongated planar ceramic body 101 as a main structure, main-surface protective layers 170 are provided on two main surfaces of the ceramic body 101, and, in the sensor element 10, the leading-end protective layer 2 is further provided outside both an end surface (a leading end surface 101e of the ceramic body 101) and four side surfaces on a side of one leading end portion. The four side surfaces other than opposite end surfaces in the longitudinal direction of the sensor element 10 (or the element base 1, or the ceramic body 101) are hereinafter simply referred to as side surfaces of the sensor element 10 (or the element base 1, or the ceramic body 101).

The ceramic body 101 is made of ceramic containing, as a main component, zirconia (yttrium stabilized zirconia), which is an oxygen-ion conductive solid electrolyte. Various components of the sensor element 10 are provided outside and inside the ceramic body 101. The ceramic body 101 having the configuration is dense and airtight. The configuration of the sensor element 10 illustrated in FIG. 1 is just an example, and a specific configuration of the sensor element 10 is not limited to this configuration.

The sensor element 10 illustrated in FIG. 1 is a so-called serial three-chamber structure type gas sensor element including a first internal chamber 102, a second internal chamber 103, and a third internal chamber 104 within the ceramic body 101. That is to say, in the sensor element 10, the first internal chamber 102 communicates, through a first diffusion control part 110 and a second diffusion control part 120, with a gas inlet 105 opening to the outside on a side of the one end portion E1 of the ceramic body 101 (to be precise, communicating with the outside through the leading-end protective layer 2), the second internal chamber 103 communicates with the first internal chamber 102 through a third diffusion control part 130, and the third internal chamber 104 communicates with the second internal chamber 103 through a fourth diffusion control part 140. A path from the gas inlet 105 to the third internal chamber 104 is also referred to as a gas distribution part. In the sensor element 10 according to the present embodiment, the distribution part is provided straight along the longitudinal direction of the ceramic body 101.

The first diffusion control part 110, the second diffusion control part 120, the third diffusion control part 130, and the fourth diffusion control part 140 are each provided as two slits vertically arranged in FIG. 1. The first diffusion control part 110, the second diffusion control part 120, the third diffusion control part 130, and the fourth diffusion control part 140 provide predetermined diffusion resistance to the measurement gas passing therethrough. A buffer space 115 having an effect of buffering pulsation of the measurement gas is provided between the first diffusion control part 110 and the second diffusion control part 120.

An outer pump electrode 141 is provided on an outer surface of the ceramic body 101, and an inner pump electrode 142 is provided in the first internal chamber 102. Furthermore, an auxiliary pump electrode 143 is provided in the second internal chamber 103, and a measurement electrode 145 as a sensing part for directly sensing a gas component to be measured is provided in the third internal chamber 104. In addition, a reference gas inlet 106 which communicates with the outside and through which a reference gas is introduced is provided on the other end portion E2 of the ceramic body 101, and a reference electrode 147 is provided in the reference gas inlet 106.

In a case where a target of measurement of the sensor element 10 is NOx in the measurement gas, for example, the concentration of a NOx gas in the measurement gas is calculated by a process as described below.

First, the measurement gas introduced into the first internal chamber 102 is adjusted to have a substantially constant oxygen concentration by a pumping action (pumping in or out of oxygen) of a main pump cell P1, and then introduced into the second internal chamber 103. The main pump cell P1 is an electrochemical pump cell including the outer pump electrode 141, the inner pump electrode 142, and a ceramic layer 101a that is a portion of the ceramic body 101 existing between these electrodes. In the second internal chamber 103, oxygen in the measurement gas is pumped out of the element by a pumping action of an auxiliary pump cell P2 that is also an electrochemical pump cell, so that the measurement gas is in a sufficiently low oxygen partial pressure state. The auxiliary pump cell P2 includes the outer pump electrode 141, the auxiliary pump electrode 143, and a ceramic layer 101b that is a portion of the ceramic body 101 existing between these electrodes.

The outer pump electrode 141, the inner pump electrode 142, and the auxiliary pump electrode 143 are each formed as a porous cermet electrode (e.g., a cermet electrode made of $ZrO_2$ and Pt that contains Au of 1%). The inner pump electrode 142 and the auxiliary pump electrode 143 to be in contact with the measurement gas are each formed using a material having weakened or no reducing ability with respect to a NOx component in the measurement gas.

NOx in the measurement gas caused by the auxiliary pump cell P2 to be in the low oxygen partial pressure state is introduced into the third internal chamber 104, and reduced or decomposed by the measurement electrode 145 provided in the third internal chamber 104. The measurement electrode 145 is a porous cermet electrode also functioning as a NOx reduction catalyst that reduces NOx existing in an atmosphere in the third internal chamber 104. During the reduction or decomposition, a potential difference between the measurement electrode 145 and the reference electrode 147 is maintained constant. Oxygen ions generated by the above-mentioned reduction or decomposition are pumped out of the element by a measurement pump cell P3. The measurement pump cell P3 includes the outer pump electrode 141, the measurement electrode 145, and a ceramic layer 101c that is a portion of the ceramic body 101 existing between these electrodes. The measurement pump cell P3 is an electrochemical pump cell pumping out oxygen generated by decomposition of NOx in an atmosphere around the measurement electrode 145.

Pumping (pumping in or out of oxygen) of the main pump cell P1, the auxiliary pump cell P2, and the measurement pump cell P3 is achieved, under control performed by the controller 50, by the pump cell power supply (variable power supply) 30 applying a voltage necessary for pumping between electrodes included in each of the pump cells. In a case of the measurement pump cell P3, a voltage is applied between the outer pump electrode 141 and the measurement electrode 145 so that the potential difference between the measurement electrode 145 and the reference electrode 147 is maintained at a predetermined value. The pump cell power supply 30 is typically provided for each pump cell.

The controller 50 detects a pump current Ip2 flowing between the measurement electrode 145 and the outer pump electrode 141 in accordance with the amount of oxygen pumped out by the measurement pump cell P3, and calculates a NOx concentration in the measurement gas based on a linear relationship between a current value (NOx signal) of the pump current Ip2 and the concentration of decomposed NOx.

The gas sensor 100 preferably includes a plurality of electrochemical sensor cells, which are not illustrated, sensing the potential difference between each pump electrode and the reference electrode 147, and each pump cell is controlled by the controller 50 based on a signal detected by each sensor cell.

In the sensor element 10, a heater 150 is buried in the ceramic body 101. The heater 150 is provided, below the gas distribution part in FIG. 1, over a range from the vicinity of the one end portion E1 to at least a location of formation of the measurement electrode 145 and the reference electrode 147. The heater 150 is provided mainly to heat the sensor element 10 to enhance oxygen-ion conductivity of the solid electrolyte forming the ceramic body 101 when the sensor element 10 is in use. More particularly, the heater 150 is provided to be surrounded by an insulating layer 151.

The heater 150 is a resistance heating body made, for example, of platinum. The heater 150 generates heat by being powered from the heater power supply 40 under control performed by the controller 50.

The sensor element 10 according to the present embodiment is heated by the heater 150 when being in use so that the temperature at least in a range from the first internal chamber 102 to the second internal chamber 103 becomes 500° C. or more. In some cases, the sensor element 10 is heated so that the temperature of the gas distribution part as a whole from the gas inlet 105 to the third internal chamber 104 becomes 500° C. or more. These are to enhance the oxygen-ion conductivity of the solid electrolyte forming each pump cell and to desirably demonstrate the ability of each pump cell. In this case, the temperature in the vicinity of the first internal chamber 102, which becomes the highest temperature, becomes approximately 700° C. to 800° C.

In the following description, from among the two main surfaces of the ceramic body 101, a main surface (or an outer surface of the sensor element 10 having the main surface) which is located on an upper side in FIG. 1 and is on a side where the main pump cell P1, the auxiliary pump cell P2, and the measurement pump cell P3 are mainly provided is also referred to as a pump surface, and a main surface (or an outer surface of the sensor element 10 having the main surface) which is located on a lower side in FIG. 1 and is on a side where the heater 150 is provided is also referred to as a heater surface. In other words, the pump surface is a main surface closer to the gas inlet 105, the three internal chambers, and the pump cells than to the heater 150, and the heater surface is a main surface closer to the heater 150 than to the gas inlet 105, the three internal chambers, and the pump cells.

A plurality of electrode terminals 160 are formed on the respective main surfaces of the ceramic body 101 on the other end portion E2 to establish electrical connection between the sensor element 10 and the outside. These electrode terminals 160 are electrically connected to the above-mentioned five electrodes, opposite ends of the heater 150, and a lead for detecting heater resistance, which is not illustrated, through leads provided within the ceramic body 101, which are not illustrated, to have a predetermined correspondence relationship. Application of a voltage from the pump cell power supply 30 to each pump cell of the sensor element 10 and heating by the heater 150 by being powered from the heater power supply 40 are thus performed through the electrode terminals 160.

The sensor element 10 further includes the above-mentioned main-surface protective layers 170 (170a and 170b) on the pump surface and the heater surface of the ceramic body 101. The main-surface protective layers 170 are layers made of alumina, having a thickness of approximately 5 μm to 30 μm, and including pores with a porosity of approximately 20% to 40%, and are provided to prevent adherence of any foreign matter and poisoning substances to the main surfaces (the pump surface and the heater surface) of the ceramic body 101 and the outer pump electrode 141 provided on a side of the pump surface. The main-surface protective layer 170a on the pump surface thus functions as a pump electrode protective layer for protecting the outer pump electrode 141.

In the present embodiment, the porosity is obtained by applying a known image processing method (e.g., binarization processing) to a scanning electron microscope (SEM) image of an evaluation target.

In FIG. 1, the main-surface protective layers 170 are provided over substantially all of the pump surface and the heater surface except that the electrode terminals 160 are partially exposed, but this is just an example. The main-surface protective layers 170 may locally be provided in the vicinity of the outer pump electrode 141 on the one end portion E1 compared with the case illustrated in FIG. 1.

<Details of Leading-End Protective Layer>

In the sensor element 10, the leading-end protective layer 2 is provided around an outermost periphery of the element base 1 having a configuration as described above in a predetermined range from the one end portion E1.

The leading-end protective layer 2 is provided in a manner of surrounding a portion of the element base 1 in which the temperature becomes high (up to approximately 700° C. to 800° C.) when the gas sensor 100 is in use, in order to secure water resistance in the portion to thereby suppress the occurrence of cracking (water-induced cracking) of the element base 1 due to thermal shock caused by local temperature reduction upon direct exposure of the portion to water.

In addition, the leading-end protective layer 2 is provided to secure poisoning resistance to prevent poisoning substances, such as Mg, from entering into the sensor element 10.

As illustrated in FIG. 1, in the sensor element 10 according to the present embodiment, the leading-end protective layer 2 includes two layers, an inner leading-end protective layer 22 and an outer leading-end protective layer 23. An underlying layer 3 is provided between the leading-end protective layer 2 (the inner leading-end protective layer 22) and the element base 1.

The underlying layer 3 is a layer provided to secure bonding (adhesion) of the inner leading-end protective layer 22 (further, the outer leading-end protective layer 23)

formed thereon. The underlying layer 3 is provided at least on the two main surfaces of the element base 1 on the side of the pump surface and on the side of the heater surface. That is to say, the underlying layer 3 includes an underlying layer 3a on the side of the pump surface and an underlying layer 3b on the side of the heater surface. The underlying layer 3, however, is not provided on the leading end surface 101e of the ceramic body 101 (of the element base 1).

The underlying layer 3 is made of alumina, has a porosity of 30% to 60%, and has a thickness of 15 µm to 50 µm. In contrast to the inner leading-end protective layer 22 and the outer leading-end protective layer 23, the underlying layer 3 is formed along with the element base 1 in a process of manufacturing the element base 1 as will be described later.

The inner leading-end protective layer 22 and the outer leading-end protective layer 23 are provided in this order from inside to cover the leading end surface 101e and the four side surfaces on the side of the one end portion E1 of the element base 1 (around an outer periphery of the element base 1 on the side of the one end portion E1).

The inner leading-end protective layer 22 is made of alumina, has a porosity of 45% to 60%, and has a thickness of 450 µm to 650 µm. The outer leading-end protective layer 23 is made of alumina, has a porosity of 10% to 40%, which is lower than the porosity of the inner leading-end protective layer 22, and has a thickness of 50 µm to 300 µm. The leading-end protective layer 2 thus has a configuration in which the inner leading-end protective layer 22 having a lower thermal conductivity than the outer leading-end protective layer 23 is covered with the outer leading-end protective layer 23 having a lower porosity than the inner leading-end protective layer 22. The inner leading-end protective layer 22 is provided as a low thermal conductivity layer to have a function to suppress thermal conduction from the outside to the element base 1.

The outer leading-end protective layer 23 preferably has a surface roughness (an arithmetic average roughness) Ra of 50 µm or less. In this case, an effect of suppressing heat transfer by radiation from the sensor element 10 is expected because a portion closer to metallic members has a low surface roughness.

The inner leading-end protective layer 22 and the outer leading-end protective layer 23 are formed by sequentially thermal spraying (plasma-spraying) materials for them with respect to the element base 1 having the surface on which the underlying layer 3 has been formed. This is to develop an anchoring effect between the underlying layer 3 formed in advance at the manufacture of the element base 1 and the inner leading-end protective layer 22 to thereby secure bonding (adhesion) of the inner leading-end protective layer 22 (and the outer leading-end protective layer 23 formed outside the inner leading-end protective layer 22) to the underlying layer 3. In other words, the underlying layer 3 has a function to secure bonding (adhesion) of the inner leading-end protective layer 22.

The inner leading-end protective layer 22 and the outer leading-end protective layer 23 are provided not to cover the underlying layer 3 (3a and 3b) as a whole, but are formed to expose an end portion of the underlying layer 3 on a side opposite the side of the one end portion E1 in the longitudinal direction of the sensor element 10. This is to more surely secure bonding (adhesion) of the inner leading-end protective layer 22 (and the outer leading-end protective layer 23 formed outside the inner leading-end protective layer 22) to the underlying layer 3.

In addition, in the sensor element 10 illustrated in FIG. 1, the outer leading-end protective layer 23 is formed to expose an end portion of the inner leading-end protective layer 22 on a side opposite the side of the one end portion E1, but the outer leading-end protective layer 23 is not necessarily required to be formed to expose the end portion. The outer leading-end protective layer 23 may be formed to cover the end portion of the inner leading-end protective layer 22.

<Sealing of Sensor Element and Protective Cover>

Figure 2:
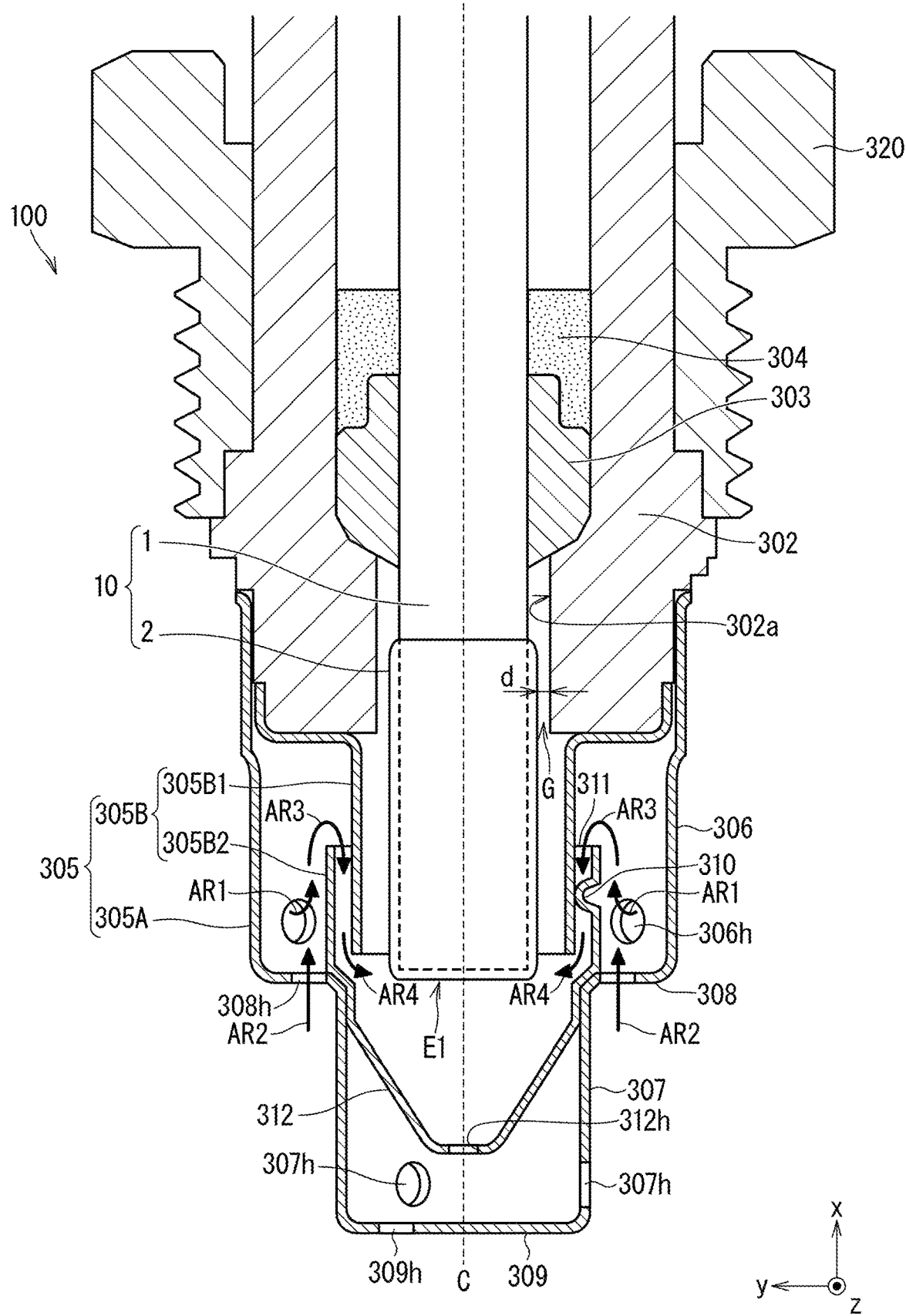
FIG. 2 illustrates a detailed configuration around (in particular, around one end portion E1 of) a sensor element 10 of the gas sensor 100.

FIG. 2 illustrates a detailed configuration around (in particular, around the one end portion E1 of) the sensor element 10 of the gas sensor 100. In the gas sensor 100 illustrated in FIG. 2, a portion of the sensor element 10 on the side of the pump surface faces the viewer in FIG. 2.

In the gas sensor 100, the sensor element 10 is housed in a housing 302 that is a hollow cylindrical member made of metal (e.g., stainless steel) excluding the vicinity of the one end portion E1 thereof, which is not illustrated in FIG. 1. More specifically, prior to housing, annular parts including a ceramic supporter 303 and a green compact 304 are mounted around an outer periphery of the sensor element 10, the housing 302 is further mounted around outer peripheries of the annular parts, and then the green compact 304 is compressed through application of an external force to thereby achieve a state in which the sensor element 10 is fixed within the housing 302 and a portion between the one end portion E1 and the other end portion E2 is sealed to be airtight. The sensor element 10 is fixed so that a central axis of the sensor element 10 coincides with a central axis C of an internal space of the cylindrical housing 302. In this case, the sensor element 10 is fixed so that a large part of a portion of the sensor element 10 in which the leading-end protective layer 2 is formed protrudes from one leading end portion (a lower end portion in a direction of the x-axis in FIG. 2) of the housing 302 downward (in a negative direction of the x-axis) in FIG. 2.

Only a single ceramic supporter 303 and a single green compact 304 are illustrated in FIG. 2 for ease of illustration, but a plurality of ceramic supporters 303 and a plurality of green compacts 304 are alternately stacked in actuality. Illustration of the leading-end protective layer 2 is also simplified in FIG. 2.

Electrical connection schematically shown in FIG. 1 between the plurality of electrode terminals 160 in the other end portion E2 and the pump cell power supply 30, the heater power supply 40, the controller 50, and the like external to the sensor element 10 is established with a portion of the sensor element 10 on the side of the other end portion E2 being inserted into an insertion opening having a contact point member of a not-illustrated contact member, which is provided above a range of illustration in FIG. 2 and is electrically connected to the heater power supply 40 and the like.

A screw nut 320 is mounted around an outer periphery of the housing 302, and the gas sensor 100 is to be screwed at a measurement location using a male threaded portion on an outer periphery of the screw nut 320.

The gas sensor 100 further includes a protective cover 305 made of metal (e.g., stainless steel). The protective cover 305 is attached to the one leading end portion of the housing 302 to surround a portion of the sensor element 10 protruding from the housing 302. The protective cover 305 has a two-layer structure of an outer protective cover 305A and an inner protective cover 305B.

The outer protective cover 305A is a portion to come into direct contact with the measurement gas when the gas sensor 100 is in use. The outer protective cover 305A is stepped in cross section, and includes a cylindrical large diameter portion 306 including a portion fixed to a lower end portion of the outer periphery of the housing 302 in FIG. 2, a closed-end cylindrical small diameter portion 307 having a smaller diameter than the large diameter portion 306, and a stepped portion 308 connecting the large diameter portion 306 and the small diameter portion 307. The large diameter portion 306 and the stepped portion 308 respectively have through holes 306h and through holes 308h to allow the measurement gas to flow into the interior of the outer protective cover 305A. The plurality of through holes 306h and the plurality of through holes 308h are provided at appropriate intervals in a circumferential direction. On the other hand, the small diameter portion 307 and a bottom 309 thereof respectively have through holes 307h and a through hole 309h to allow the measurement gas to flow from the interior to the exterior of the outer protective cover 305A. The plurality of through holes 307h are also provided at appropriate intervals in the circumferential direction.

On the other hand, the inner protective cover 305B includes a cylindrical first portion 305B1 extending from the portion fixed to the lower end portion of the housing 302 in FIG. 2 and a second portion 305B2 attached to the outside of the first portion 305B1. The second portion 305B2 has an externally swaged portion 310 to thereby be fixed to the first portion 305B1 so that a flow path 311 is formed between the first portion 305B1 and the second portion 305B2, and is retained at a corner of the small diameter portion 307 and the stepped portion 308 of the outer protective cover 305A.

A lower end portion of the first portion 305B1 in FIG. 2 is open, whereas a lower end portion of the second portion 305B2 in FIG. 2 is a tapered portion 312 having a through hole 312h in a leading end portion (lower end portion) thereof. The one end portion E1 of the sensor element 10 slightly protrudes from the lower end portion of the first portion 305B1 in FIG. 2. The distance from the one end portion E1 to the bottom 309 of the outer protective cover 305A is approximately 10 mm.

When the gas sensor 100 including the protective cover 305 having a configuration as described above is in use, the measurement gas flows into a space between the outer protective cover 305A and the inner protective cover 305B through the through holes 306h and the through holes 308h as shown by arrows AR1 and arrows AR2. The measurement gas further flows into a space inside the inner protective cover 305B in which a portion in the vicinity of the one end portion E1 of the sensor element 10 is present through the flow path 311 between the first portion 305B1 and the second portion 305B2 of the inner protective cover 305B as shown by arrows AR3 and arrows AR4.

That is to say, the protective cover 305 is a "leading end inflow" type protective cover configured to allow the measurement gas to flow into the interior thereof from a portion of the protective cover 305 on the side of the one end portion E1 of the sensor element 10 located within the protective cover 305.

The measurement gas inside the inner protective cover 305B is discharged to the outside through the through hole 312h and further through the through holes 307h and the through hole 309h as appropriate.

<Suppression of Heater Power>

As described above, the sensor element 10 is heated by the heater 150 when being in use so that the temperature at least in the range from the first internal chamber 102 to the second internal chamber 103 becomes 500° C. or more to enhance the oxygen-ion conductivity of the solid electrolyte forming each pump cell and to desirably demonstrate the ability of each pump cell. In this case, the temperature in the vicinity of the first internal chamber 102, which becomes the highest temperature, becomes approximately 700° C. to 800° C.

In terms of extension of the life of the heater 150, each portion of the sensor element 10 described above is preferably heated at minimum heater power (power applied to the heater 150). It is thus required to transfer minimum heat generated by the heater 150 to the outside of the sensor element 10 and further to the outside of the gas sensor 100.

In this respect, a portion of the sensor element 10 to be, in particular, heated by the heater 150 to a high temperature when being in use is surrounded by the metallic members (metallic parts), such as the housing 302 and the protective cover 305, as illustrated in FIG. 2. At heating by the heater 150, radiation from these metallic members produces the heat retaining effect. In terms of suppression of heater power, it is preferable to more suitably obtain the heat retaining effect produced by the radiation.

In light of the foregoing, in the gas sensor 100 according to the present embodiment, the distance (a minimum distance) between the sensor element 10 and a metallic member closest to the sensor element 10 is set to 0.95 mm or less. In a case illustrated in FIG. 2, the metallic member closest to the sensor element 10 is the housing 302, and the sensor element 10 and the housing 302 become closest to each other at a gap G between a portion of the leading-end protective layer 2 covering a side surface (a surface parallel to a zx plane) of the sensor element 10 and an inner surface 302a of the housing 302, so that a distance d between the sensor element 10 and the housing 302 at the gap G is set to 0.95 mm or less. However, the protective cover 305 may be closer to the sensor element 10 than the housing 302 is, and, in this case, the distance between the sensor element 10 and the protective cover 305 is set to 0.95 mm or less.

The distance between the sensor element 10 and the metallic member can be set to 0.95 mm or less by reducing an inner diameter of the metallic member or by increasing the thickness of the leading-end protective layer 2.

In addition, an inner surface (a surface facing the sensor element 10) of at least a portion of the metallic member (the housing 302 in the case illustrated in FIG. 2) closest to the sensor element 10 is set to have an arithmetic average roughness Ra of 5 µm or less. The arithmetic average roughness is hereinafter also simply referred to as an inner-surface roughness.

When at least these requirements are met, heater power when the gas sensor 100 is in use is desirably suppressed in the gas sensor 100.

In terms of clearance at assembly, however, the distance between the sensor element 10 and the metallic member is preferably 0.20 mm or more.

As described above, a portion of the sensor element 10 on the one end portion E1 is covered with the leading-end protective layer 2 having the two-layer configuration. The inner leading-end protective layer 22 of the leading-end protective layer 2 mainly for thermal insulation is provided to have a porosity of 45% to 60% and have a thickness of 450 µm to 650 µm. This is mainly to secure water resistance and further to secure thermal shock resistance, but produces a certain effect of suppressing heater power.

As described above, according to the present embodiment, the gas sensor is configured so that the distance between the sensor element and the metallic member closest to the sensor element at the gap therebetween is 0.95 mm or less, and the metallic member has an inner-surface roughness Ra of 5 µm or less. The effect of retaining heat of the sensor element produced by radiation from the metallic member is thereby desirably obtained at heating of the sensor element to a predetermined driving temperature by the heater located within the sensor element when the gas sensor is in use, so that power of the heater required at heating is suppressed, and the life of the heater and further the life of the gas sensor is extended.

<Modifications>

The above-mentioned embodiment is targeted at a sensor element having three internal chambers, but the sensor element is not necessarily required to have a three-chamber structure. That is to say, the sensor element may have one internal chamber or two internal chambers.

In the above-mentioned embodiment, the inner leading-end protective layer 22 and the outer leading-end protective layer are each made of alumina, and alumina powder is used as a thermal spraying material at formation of both of the layers, but they are not necessarily required to be made of alumina. The inner leading-end protective layer 22 and the outer leading-end protective layer 23 may be made of metallic oxide, such as zirconia ($ZrO_2$), spinel ($MgAl_2O_4$), and mullite ($Al_6Ol_3Si_2$), in place of alumina. In this case, powder of the metallic oxide may be used as the thermal spraying material.

EXAMPLES

Many gas sensors 100 each having the configuration illustrated in FIG. 2 and having different combinations of the distance d between the sensor element 10 and the housing 302 and the inner-surface roughness Ra of the housing 302 were manufactured, and the influence of each value on heater power was confirmed.

Specifically, 13 gas sensors, 16 gas sensors, five gas sensors, 12 gas sensors, and 13 gas sensors respectively having five different values of the distance d of 0.78 mm, 0.92 mm, 0.95 mm, 1.02 mm, and 1.05 mm by having different combinations of the inner diameter of the housing 302 and the thickness of the leading-end protective layer 2 while each having an inner-surface roughness Ra of the housing 302 of about 5 µm were manufactured. In addition, gas sensors having values of the inner-surface roughness Ra of the housing 302 of about 0.1 µm, 0.5 µm, 1.0 µm, 7.5 µm, and 10 µm while each having a value of the distance d of 0.95 mm were manufactured one for each of the values of the inner-surface roughness Ra.

For each of the gas sensors 100, the sensor element 10 was heated by the heater 150 while the temperature (a maximum temperature reached) of the element was set to 850° C., and heater power at the time was measured.

FIG. 3 is a distribution chart having the distance d between the sensor element 10 and the housing 302 along the horizontal axis and heater power along the vertical axis to show the relationship among the distance d, the inner-surface roughness Ra of the housing 302, and heater power.

It can be seen from FIG. 3 that heater power is approximately 6 W to 7 W in a case where the distance d is in a range of 0.95 mm or less and the inner-surface roughness Ra is about 5 µm or less, whereas heater power is approximately 7 W at the minimum in a case where one of the requirements is not met.

The results show that heater power is reduced by configuring the gas sensor so that the distance d is 0.95 mm or less and the inner-surface roughness Ra is 5 µm or less.

While the invention has been shown and described in detail, the foregoing description is in all aspects illustrative and not restrictive. It is therefore understood that numerous modifications and variations can be devised without departing from the scope of the invention.

What is claimed is:

1. A gas sensor sensing a sensing target gas component contained in a measurement gas and identifying concentration of said sensing target gas component, said gas sensor comprising:
    a sensor element having a central axis and an inlet for said measurement gas on one end portion, and including:
        an element base made of an oxygen-ion conductive solid electrolyte;
        a heater buried in said element base; and
        a porous leading-end protective layer covering a predetermined range of said element base on said one end portion; and
    a metallic member within which said sensor element is fixedly disposed, wherein
    a minimum distance between said sensor element and an inner surface of said metallic member is 0.20 mm or more and 0.95 mm or less, said inner surface of said metallic member being parallel to said central axis of the sensor element, and
    a portion of said inner surface of said metallic member closest to said sensor element and facing said porous leading-end protective layer in a direction perpendicular to said central axis has an arithmetic average roughness of 5 µm or less.

2. The gas sensor according to claim 1, wherein said metallic member further includes:
    a metallic housing within which said sensor element is fixed; and
    a metallic protective cover attached to said housing, and surrounding a portion of said sensor element on said one end portion to allow said measurement gas to flow into an interior of said protective cover, and
    said minimum distance is a distance between an inner surface of said housing and said sensor element.

3. The gas sensor according to claim 2, wherein said leading-end protective layer further includes:
    an inner leading-end protective layer disposed to cover said one end portion and four side surfaces of said element base continuous with said one end portion; and
    an outer leading-end protective layer disposed to cover said inner leading-end protective layer, and having a lower porosity than said inner leading-end protective layer, and
    said inner leading-end protective layer has a thickness of 450 µm or more and 650 µm or less, and has a porosity of 45% to 60%.

4. The gas sensor according to claim 3, wherein said outer leading-end protective layer has an arithmetic average roughness of 50 µm or less.

5. The gas sensor according to claim 1, wherein said leading-end protective layer further includes:
    an inner leading-end protective layer disposed to cover said one end portion and four side surfaces of said element base continuous with said one end portion; and
    an outer leading-end protective layer disposed to cover said inner leading-end protective layer, and having a lower porosity than said inner leading-end protective layer, and
    said inner leading-end protective layer has a thickness of 450 µm or more and 650 µm or less, and has a porosity of 45% to 60%.

6. The gas sensor according to claim 5, wherein
said outer leading-end protective layer has an arithmetic average roughness of 50 µm or less.

7. The gas sensor according to claim 1, wherein said portion of said inner surface of said metallic member closest to said sensor element is spaced from said porous leading-end protective layer by a gap.

8. A gas sensor sensing a sensing target gas component contained in a measurement gas and identifying concentration of said sensing target gas component, said gas sensor comprising:
   a sensor element having a central axis and an inlet for said measurement gas on one end portion, and including:
      an element base made of an oxygen-ion conductive solid electrolyte;
      a heater buried in said element base; and
      a porous leading-end protective layer covering a predetermined range of said element base on said one end portion;
   a metallic housing within which said sensor element is fixed; and
   a metallic protective cover attached to said housing, and surrounding a portion of said sensor element on said one end portion to allow said measurement gas to flow into an interior of said protective cover, wherein
   a minimum distance between one of an inner surface of said housing and an inner surface of said protective cover closer to said sensor element and said sensor element is 0.20 mm or more and 0.95 mm or less, said one of said inner surface of said housing and said inner surface of said protective cover closer to said sensor element being parallel to said central axis of the sensor element, and
   said one of said inner surface of said housing and said inner surface of said protective cover closer to said sensor element and facing said porous leading-end protective layer in a direction perpendicular to said central axis has an arithmetic average roughness of 5 µm or less.

9. The gas sensor according to claim 8, wherein
said inner surface of said housing is closer to said sensor element than is said inner surface of said protective cover.

10. The gas sensor according to claim 9, wherein
said leading-end protective layer further includes:
   an inner leading-end protective layer disposed to cover said one end portion and four side surfaces of said element base continuous with said one end portion; and
   an outer leading-end protective layer disposed to cover said inner leading-end protective layer, and having a lower porosity than said inner leading-end protective layer, and
said inner leading-end protective layer has a thickness of 450 µm or more and 650 µm or less, and has a porosity of 45% to 60%.

11. The gas sensor according to claim 10, wherein
said outer leading-end protective layer has an arithmetic average roughness of 50 µm or less.

12. The gas sensor according to claim 8, wherein
said leading-end protective layer further includes:
   an inner leading-end protective layer disposed to cover said one end portion and four side surfaces of said element base continuous with said one end portion; and
   an outer leading-end protective layer disposed to cover said inner leading-end protective layer, and having a lower porosity than said inner leading-end protective layer, and
said inner leading-end protective layer has a thickness of 450 µm or more and 650 µm or less, and has a porosity of 45% to 60%.

13. The gas sensor according to claim 12, wherein
said outer leading-end protective layer has an arithmetic average roughness of 50 µm or less.

14. The gas sensor according to claim 8, wherein said portion of said inner surface of said metallic housing closer to said sensor element is spaced from said porous leading-end protective layer by a gap.

* * * * *